(12) United States Patent  
Kaji et al.

(10) Patent No.: US 8,156,830 B2  
(45) Date of Patent: Apr. 17, 2012

(54) PHOTOSTABILITY TEST SYSTEM

(75) Inventors: Ryuichi Kaji, Osaka (JP); Satoshi Koide, Osaka (JP); Kenji Matsushita, Osaka (JP)

(73) Assignee: Nagano Science Co., Ltd. (JP)

( * ) Notice: Subject to any disclaimer, the term of this patent is extended or adjusted under 35 U.S.C. 154(b) by 364 days.

(21) Appl. No.: 12/516,320

(22) PCT Filed: Nov. 5, 2007

(86) PCT No.: PCT/JP2007/071493  
§ 371 (c)(1),  
(2), (4) Date: May 26, 2009

(87) PCT Pub. No.: WO2008/062658  
PCT Pub. Date: May 29, 2008

(65) Prior Publication Data  
US 2010/0000344 A1    Jan. 7, 2010

(30) Foreign Application Priority Data  
Nov. 24, 2006    (JP) .................... 2006-317548

(51) Int. Cl.  
*G01D 1/00* (2006.01)  
(52) U.S. Cl. ...................... 73/865.8; 356/121  
(58) Field of Classification Search ............. 73/865.8; 356/121; 362/84, 217.01, 225  
See application file for complete search history.

(56) References Cited

U.S. PATENT DOCUMENTS

| | | | | |
|---|---|---|---|---|
| 5,206,518 A | * | 4/1993 | Fedor et al. | 250/504 R |
| 5,726,705 A | * | 3/1998 | Imanishi et al. | 348/92 |
| 6,223,071 B1 | * | 4/2001 | Lundahl et al. | 600/476 |
| 6,720,562 B2 | * | 4/2004 | Rathod et al. | 250/395 |
| 7,055,976 B2 | * | 6/2006 | Blanford | 362/16 |
| 7,241,026 B2 | * | 7/2007 | Lescourret et al. | 362/240 |
| 2004/0149922 A1 | * | 8/2004 | Rathod et al. | 250/372 |
| 2005/0231956 A1 | * | 10/2005 | Lescourret et al. | 362/296 |
| 2008/0049432 A1 | * | 2/2008 | Benoit et al. | 362/326 |

FOREIGN PATENT DOCUMENTS

| JP | 61-258144 A | 11/1986 |
|---|---|---|
| JP | S61-258144 A | 11/1986 |
| JP | 03-028359 Y2 | 6/1991 |
| JP | H04-369465 A | 12/1992 |
| JP | H09-210911 A | 8/1997 |
| JP | 2002-117707 A | 4/2002 |
| JP | 2003-014615 A | 1/2003 |
| JP | 2004-301536 A | 10/2004 |
| JP | 2006-250584 A | 9/2006 |

OTHER PUBLICATIONS

International Search Report, PCT/JP2007/071493, Dec. 11, 2007.

* cited by examiner

*Primary Examiner* — Eric S McCall  
(74) *Attorney, Agent, or Firm* — Studebaker & Brackett PC; Donald R. Studebaker

(57) ABSTRACT

A plurality of fluorescent lamps 30 are in a decentered layout so as to be placed in a peripheral part of an upper space of an environmental test chamber 11 above a sample loading surface 21. The irradiance distribution of light from the fluorescent lamps 30 over the sample loading surface 21 is in the range of ±25% relative to the irradiance at the center of the sample loading surface 21.

2 Claims, 8 Drawing Sheets

FIG.4
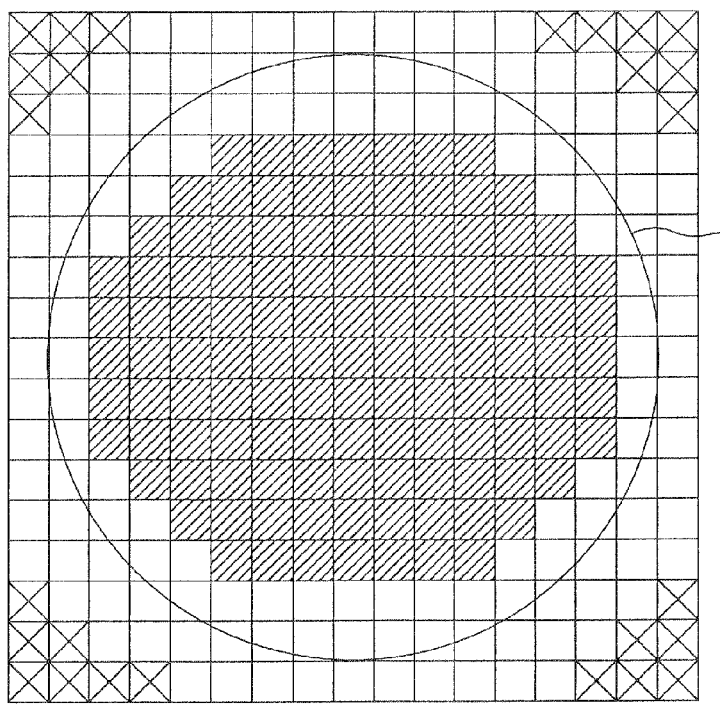
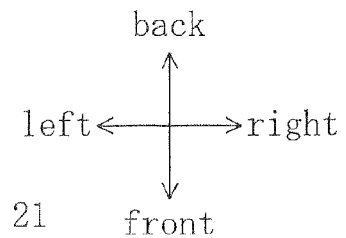
FIG.5
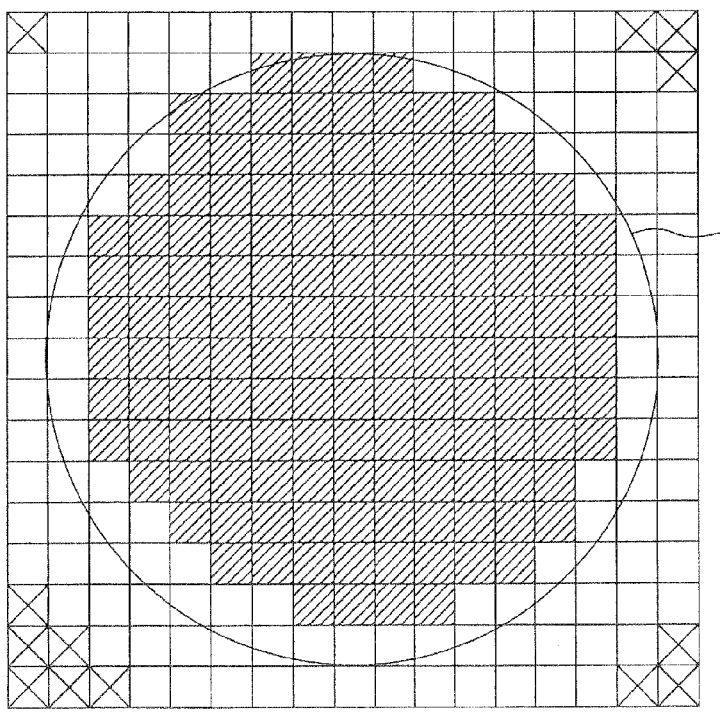
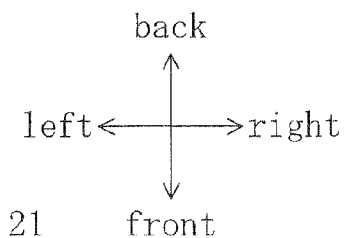

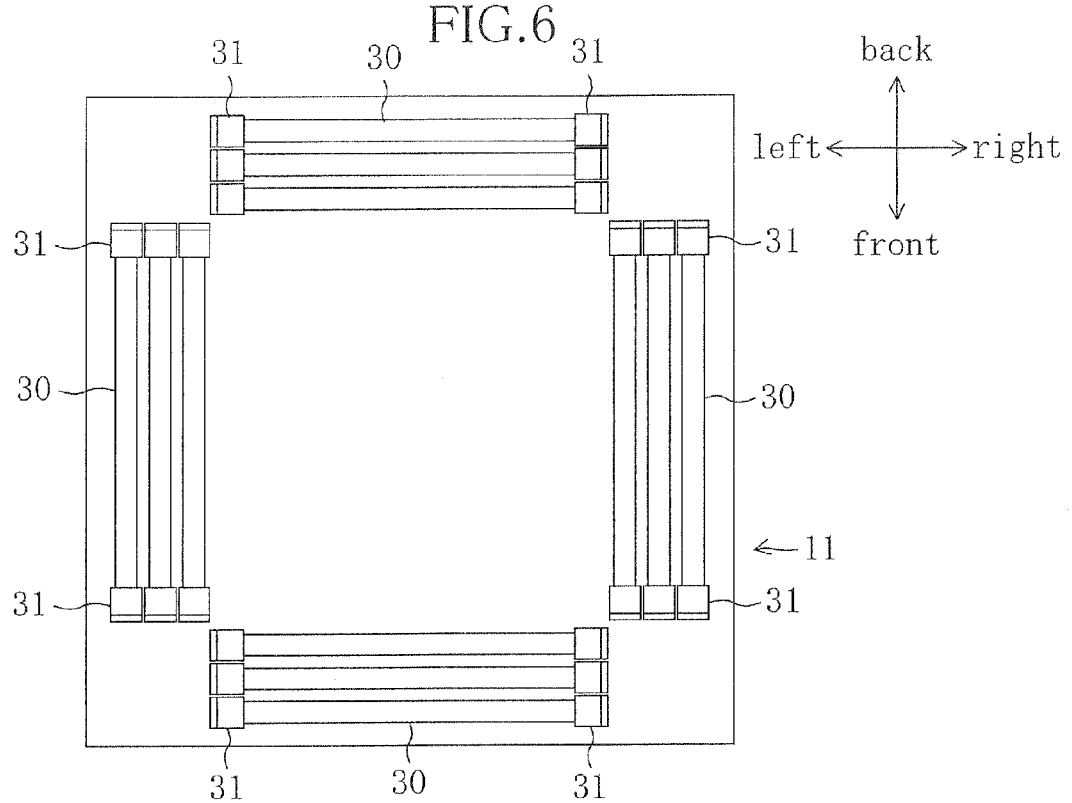
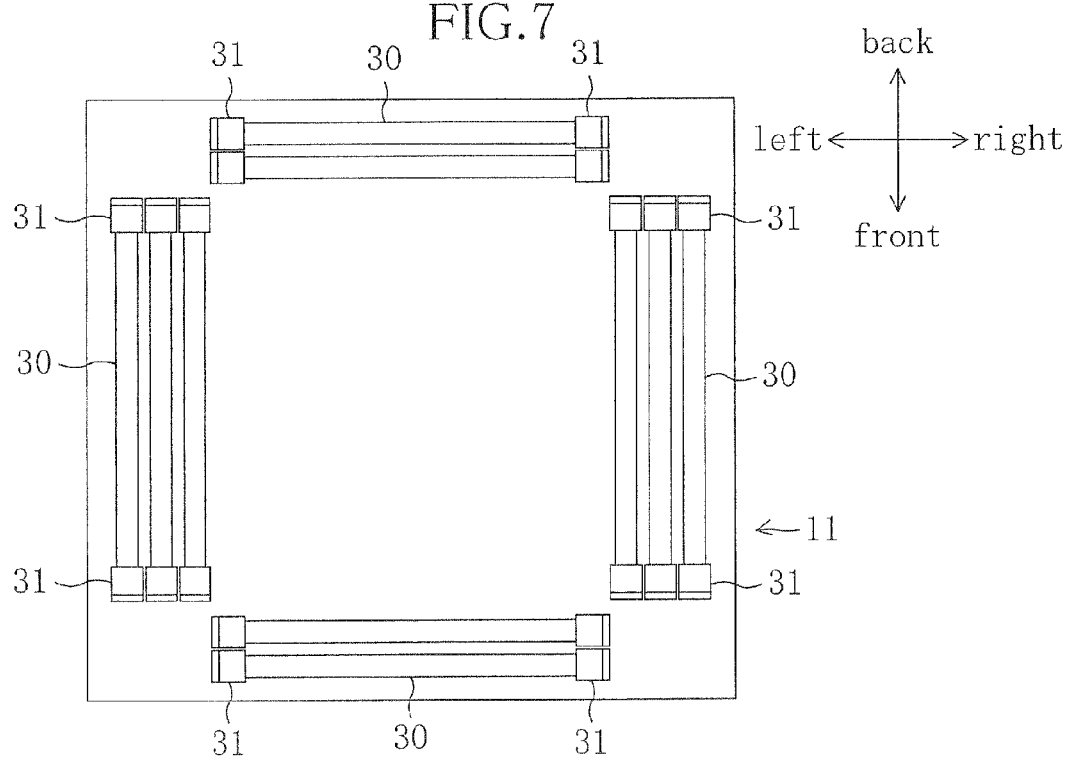

PHOTOSTABILITY TEST SYSTEM

TECHNICAL FIELD

The present invention relates to a photostability test system and specifically to the technique of achieving uniform irradiance distribution of light from fluorescent lamps over a sample loading surface.

BACKGROUND ART

A photostability test system which has an environmental test chamber for a photostability test of pharmaceutical preparations, and the like, is conventionally known (see, for example, Patent Document 1). The photostability test system disclosed in this document includes a plurality of linear fluorescent lamps placed side by side in the upper part of the environmental test chamber that is in the form of a box and a sample table, such as a turn table, in the lower part of the environmental test chamber.

The fluorescent lamps emit light to samples loaded on a sample loading surface that rotates during a test such that the sample is uniformly irradiated with the light.

Patent Document 1: Japanese Laid-Open Patent Publication No. 2003-14615

DISCLOSURE OF INVENTION

Problems to be Solved by the Invention

A photostability test system of this type has a probability that the irradiance distribution of light from fluorescent lamps over a sample loading surface is nonuniform and precise photostability test results cannot be obtained in some sample loaded positions on the sample loading surface. The distribution of irradiance is described below.

FIG. 14 is a plan view showing a layout of fluorescent lamps in a conventional photostability test system. Note that, in FIG. 14, directions of the front side, the back side, and the right and left sides of the system are defined as indicated by the arrows.

Referring to FIG. 14, a plurality of linear fluorescent lamps 30 are provided in the upper space of an environmental test chamber 11 such that the longitudinal direction of the fluorescent lamps 30 is coincident with the depth direction (from front to back) of the system and that the fluorescent lamps 30 are placed side by side in the width direction (from side to side) of the system. The fluorescent lamps 30 are staggered such that every other couple of lamps are shifted in phase in the system depth direction. This layout enables more fluorescent lamps 30 to be installed in a limited space, without deteriorating the installation density due to sockets 31, as compared with a layout where the fluorescent lamps 30 are aligned side by side in the width direction without being staggered.

FIG. 15 is a plan view showing the irradiance distribution of light from the fluorescent lamps over the sample loading surface of the conventional photostability test system. In FIG. 15, the sample loading surface 21 and its surrounding region are divided into a plurality of blocks in each of which the irradiance was measured. In this example, the size of one block is 50 mm×50 mm. Note that in FIG. 15 shaded boxes represent blocks in which the irradiance is in the range of ±10% relative to the irradiance at the center of the sample loading surface 21, crossed boxes represent blocks in which the irradiance is in the range of ±25% or more relative to the irradiance at the center, and open boxes (not shaded or not crossed) represent blocks in which the irradiance ranges from ±10% to ±25% relative to the irradiance at the center.

As seen from FIG. 15, in the conventional photostability test system, the irradiance is higher in the central region of the sample loading surface 21 and decreases toward the periphery of the sample loading surface 21. Specifically, the blocks with the irradiance range of ±10% occur with an oval distribution whose major axis extends in the system depth direction. Blocks with the irradiance range of ±25% or more relative to the irradiance at the center occur at the periphery of the sample loading surface 21, in particular at part of the periphery near the right and left sides of the system.

It is considered that this is because rays of light uniformly emitted from the fluorescent lamps 30 placed side by side overlap in the central region of the sample loading surface 21, while rays of light from the fluorescent lamps 30 reaching the periphery of the sample loading surface 21 have different intensities.

The difference in light intensity is now specifically described with attention to the blocks on the right side of the system. Rays of light from some of the fluorescent lamps 30 on the right side of the system, immediately above the right side blocks, have stronger light intensity because they fall directly below on the right side blocks. Meanwhile, rays of light from other fluorescent lamps 30 on the left side of the system are attenuated before reaching the right side blocks to provide weaker light intensity. These rays of light reaching the right side blocks also overlap but the light intensity of the overlapping rays of light on the right side blocks is weaker than the light intensity of rays overlapping in the central region of the sample loading surface 21.

Such an uneven irradiance distribution is undesirable because the results of the photostability test may vary depending on the positions of samples over the sample loading surface 21.

The present invention was conceived in view of the above circumstances and an object of the present invention is to achieve uniform irradiance distribution of light from fluorescent lamps over a sample loading surface.

Means for Solving the Problems

The invention of claim 1 is directed to a photostability test system including:

a system enclosure which has an environmental test chamber in the form of a box;

a sample table provided in a lower part of the environmental test chamber, the sample table having a sample loading surface on which a sample is to be loaded;

a plurality of fluorescent lamps provided in an upper part of the environmental test chamber, the fluorescent lamps being placed above the sample loading surface and directed toward the sample loading surface for irradiating a sample loaded on the sample loading surface, wherein the plurality of fluorescent lamps are in a decentered layout so as to be placed in a peripheral part of an upper space of the environmental test chamber above the sample loading surface such that an irradiance distribution of light from the fluorescent lamps over the sample loading surface is in the range of ±25% relative to an irradiance at a center of the sample loading surface.

In the invention of claim 1, the plurality of fluorescent lamps are in a decentered layout so as to be placed in a peripheral part of the upper space of the environmental test chamber above the sample loading surface. The irradiance distribution of light from the fluorescent lamps over the sample loading surface is in the range of ±25% relative to the irradiance at a center of the sample loading surface.

The invention is characterized in that the plurality of fluorescent lamps are symmetrical with respect to at least any one of a depth direction and a width direction in a plane.

The invention is characterized in that the plurality of fluorescent lamps are rotationally symmetrical by 90° or 180° in a plane.

In the invention, the plurality of fluorescent lamps are symmetrical with respect to at least any one of a depth direction and a width direction in a plane or are rotationally symmetrical by 90° or 180° in a plane.

The invention is characterized in that a side wall of the environmental test chamber is formed by a reflector which has a light reflectance of 20% or higher.

In the invention, the reflector which forms the side wall of the environmental test chamber reflects 20% or more of the rays of light emitted by the fluorescent lamps, and both the primary and secondary reflections are applied to the samples S.

The invention is characterized in that the fluorescent lamps have a linear shape.

The invention is characterized in that the fluorescent lamps have a circular shape.

The invention is characterized in that the fluorescent lamps have a dot shape.

In the inventions, the photostability test is carried out using various shapes of fluorescent lamps, such as linear, circular, dot, etc.

Effects of the Invention

Thus, according to the present invention, a plurality of fluorescent lamps are in a decentered layout so as to be placed in a peripheral part of the upper space of the environmental test chamber above the sample loading surface. With this layout, the irradiance distribution of light from the fluorescent lamps over the sample loading surface is within the irradiance range of ±25% relative to the irradiance at the center of the sample loading surface, and hence, the irradiance distribution over the sample loading surface is uniform. Therefore, a variation in irradiance, which would be caused according to the sample loaded positions over the sample loading surface, can be prevented, and the photostability test can be carried out more precisely, improving the reliability of the test.

Also, the side walls of the environmental test chamber are formed by the reflectors which have light reflectance of 20% or higher, rays of light emitted by the fluorescent lamps are reflected by the reflectors, and both the primary and secondary reflections are appropriately applied to the samples. This feature is advantageous in achieving more uniform irradiance distribution.

BRIEF DESCRIPTION OF DRAWINGS

FIG. 4 illustrates the irradiance distribution of light from the fluorescent lamps over a sample loading surface.

FIG. 5 illustrates the irradiance distribution of light from the fluorescent lamps over a sample loading surface in another example where the side walls of an environmental test chamber have improved reflectance.

FIG. 6 is a plan view of another embodiment, showing a layout example of fluorescent lamps.

FIG. 7 is a plan view of still another embodiment, showing a layout example of fluorescent lamps.

Figure 1:
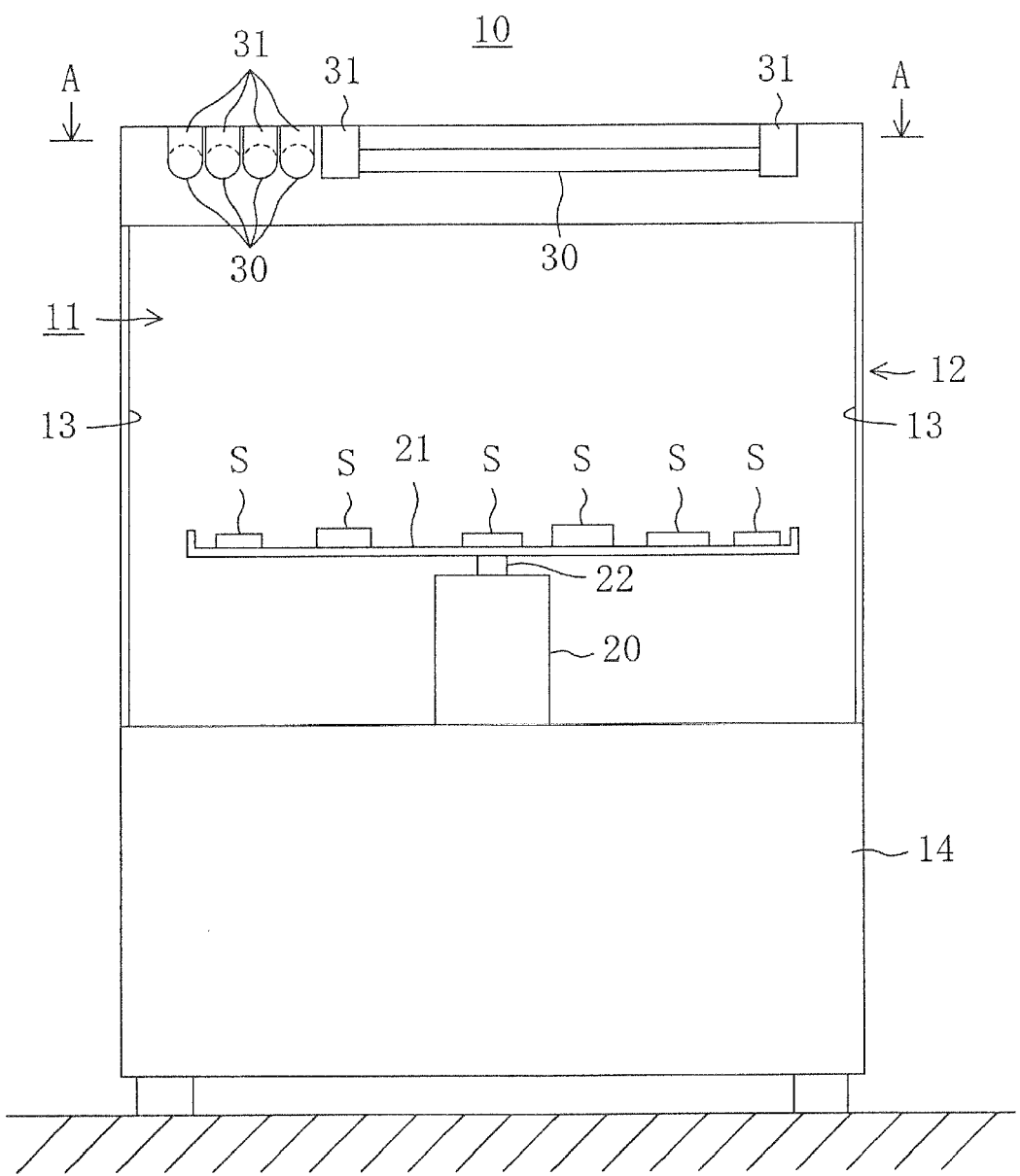
FIG. 1 is a front view of a photostability test system according to an embodiment of the present invention which schematically shows its structure.

DESCRIPTION OF REFERENCE NUMERALS 10 photostability test system
11 environmental test chamber
12 system enclosure
13 reflector
20 sample table
21 sample loading surface
30 fluorescent lamps

BEST MODE FOR CARRYING OUT THE INVENTION

Hereinafter, embodiments of the present invention are described with reference to the drawings. The following description of preferred embodiments is merely exemplary in nature and is not intended to limit the invention or the application and uses of the invention.

FIG. 1 is a front view of a photostability test system according to an embodiment of the present invention which schematically shows its structure. Referring to FIG. 1, the photostability test system 10 includes a system enclosure 12 which has an environmental test chamber 11 in the form of a box, a sample table 20 provided in the lower part of the environmental test chamber 11, the sample table 20 having a sample loading surface 21 in its upper face on which samples S are to be loaded, and a plurality of fluorescent lamps 30 provided in the upper part of the environmental test chamber 11, the fluorescent lamps 30 being placed above the sample loading surface 21 and directed toward the sample loading surface 21 for irradiating the samples S loaded on the sample loading surface 21.

The system enclosure 12 has a door (not shown) in the front face of the system enclosure which can be opened and closed. The environmental test chamber 11 can be opened or closed by opening or closing the door. In the environmental test chamber 11, the fluorescent lamps 30 emit rays of light including UV toward the samples S loaded on the sample loading surface 21, such as pharmaceutical preparations, for the test of photostability of the samples S. With this system, photostability test data which are necessary for application for drug manufacturing approval can be obtained.

The side walls of the environmental test chamber 11 may be formed by reflectors 13 which have reflectance of 20% or higher for the rays emitted by the fluorescent lamps 30. In this embodiment, the reflectors 13 are stainless B2 plates.

The photostability test system may further include a controller 14 in the lower part of the environmental test chamber 11 of the system enclosure 12 for controlling, for example, the temperature or humidity conditions in the environmental test chamber 11 or the irradiance or UV intensity of the fluorescent lamps 30.

The sample table 20 has the sample loading surface 21 on which the samples S are to be loaded, and the sample loading surface 21 is rotatable on a rotation shaft 22. The rotation shaft 22 is spun by a motor (not shown) encased in the sample table 20.

The present invention is not limited to the rotatable sample loading surface 21 of the sample table 20 of the present embodiment. For example, the sample loading surface 21 may not be rotatable but simply placed on the sample table 20.

The plurality of fluorescent lamps 30 emit rays of light including UV toward the samples S. The fluorescent lamps 30 have a linear shape and have connector plugs (not shown) at both ends. The fluorescent lamps 30 are installed in the upper space of the environmental test chamber 11 by inserting the connector plugs into sockets 31 mounted on the ceiling of the environmental test chamber 11.

Figure 2:
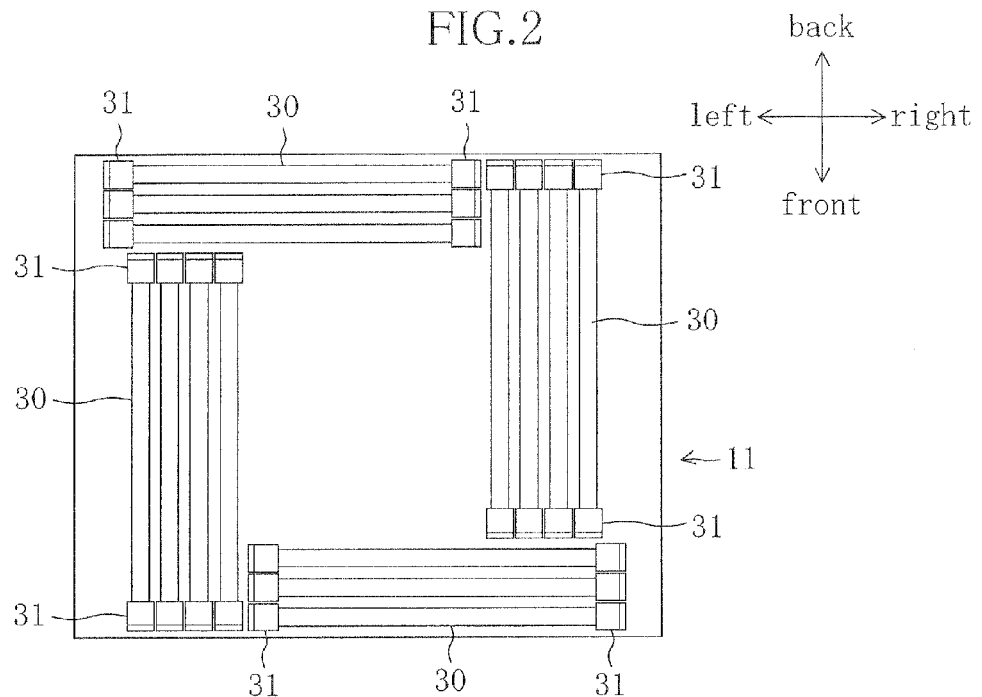
FIG. 2 is a cross-sectional view of the photostability test system taken along line A-A, showing a layout example of fluorescent lamps.

FIG. 2 is a cross-sectional view of the photostability test system taken along line A-A, showing a layout example of the fluorescent lamps. In FIG. 2, directions of the front side, the back side, and the right and left sides of the system are defined as indicated by the arrows.

Referring to FIG. 2, the plurality of fluorescent lamps 30 are in a decentered layout so as to be placed in a peripheral part of an upper space above the sample loading surface 21. Specifically, four linear fluorescent lamps 30 are installed on the left side of the environmental test chamber 11 such that the longitudinal direction of the fluorescent lamps 30 is coincident with the system depth direction and that the fluorescent lamps 30 are placed side by side in the system width direction. The length of these fluorescent lamps 30 is shorter than the depth of the environmental test chamber 11. The front side ends of the respective fluorescent lamps 30 are positioned near the front face of the system such that there is some gap between the back side ends of the fluorescent lamps 30 and the back face of the system.

Likewise, another four linear fluorescent lamps 30 are installed on the right side of the environmental test chamber 11 such that the longitudinal direction of the fluorescent lamps 30 is coincident with the system depth direction and that the fluorescent lamps 30 are placed side by side in the system width direction. The back side ends of the respective fluorescent lamps 30 are positioned near the back face of the system such that there is some gap between the front side ends of the fluorescent lamps 30 and the front face of the system.

The fluorescent lamps 30 installed on the right and left sides of the environmental test chamber 11 are in different phases with respect to the system depth direction.

The gaps between these fluorescent lamps 30 and the front and back faces of the system are each occupied by three fluorescent lamps 30 placed side by side such that the longitudinal direction of the fluorescent lamps 30 is coincident with the system width direction.

Among the fluorescent lamps 30 extending in the width direction, the fluorescent lamps 30 placed in the gap on the front side of the system are positioned such that the left side ends of the fluorescent lamps 30 are near the front side ends of the fluorescent lamps 30 extending in the depth direction on the left side of the system.

The other fluorescent lamps 30 extending in the width direction and placed in the gap on the back side of the system are positioned such that the right side ends of the fluorescent lamps 30 are near the back side ends of the fluorescent lamps 30 extending in the depth direction on the right side of the system.

Such an arrangement of the fluorescent lamps 30 results in a square "F" layout where the fluorescent lamps 30 are placed in a peripheral region, i.e., excluding the central region of the sample loading surface 21. In this case, the fluorescent lamps 30 are rotationally symmetrical by 180° in a plane.

Figure 3:
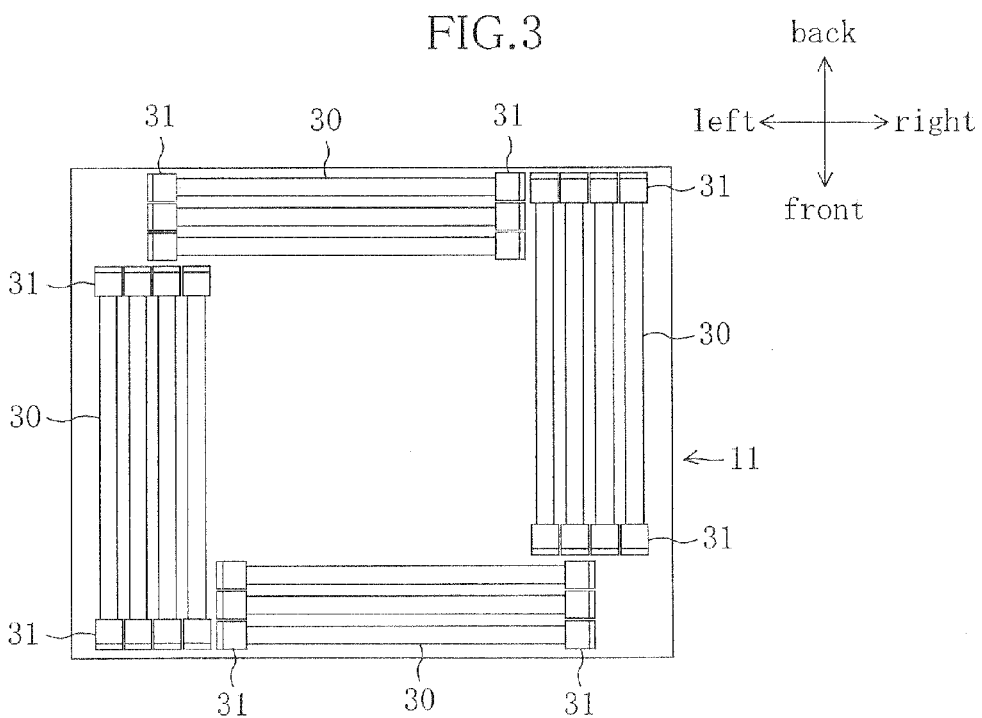
FIG. 3 is a cross-sectional view of the photostability test system taken along line A-A, showing another layout example of fluorescent lamps.

The layout shown in FIG. 2 is such a square "□" layout that the fluorescent lamps 30 extending in the system depth direction do not exceed the both ends of the fluorescent lamps 30 extending in the system width direction, to which the present invention however is not limited. For example, the fluorescent lamps 30 extending in the system depth direction may be shifted toward the right and left walls as shown in FIG. 3 such that the open area in the square "□" layout is enlarged.

FIG. 4 illustrates the irradiance distribution of light from the fluorescent lamps over the sample loading surface in the photostability test system of the present embodiment. In FIG. 4, the sample loading surface 21 and its surrounding region are divided into a plurality of blocks in each of which the irradiance was measured. In this example, the size of one block is 50 mm×50 mm. Note that shaded boxes represent blocks in which the irradiance is in the range of ±10% relative to the irradiance at the center of the sample loading surface 21, and crossed boxes represent blocks in which the irradiance is in the range of ±25% or more relative to the irradiance at the center.

As seen in FIG. 4, in the photostability test system 10 of the present embodiment, the blocks with the irradiance range of ±10% relative to the irradiance at the center of the sample loading surface 21 occur with a generally-oval distribution around the center of the sample loading surface 21, more strictly, an oval distribution with the major axis extending in the width direction and being slightly longer than the minor axis. Blocks with the irradiance range of ±25% or more relative to the irradiance at the center occur only at the four corners of the measured field. Thus, the irradiance distribution over the sample loading surface 21 is within the irradiance range of ±25%, which means the irradiance distribution of light from the fluorescent lamps is uniform over the sample loading surface 21.

FIG. 5 illustrates the irradiance distribution of light from the fluorescent lamps over the sample loading surface in another example where the side walls of the environmental test chamber of the photostability test system of the present embodiment have improved light reflectance. In the example of FIG. 4, the side walls of the environmental test chamber 11 are stainless B2 plates. In the example of FIG. 5, the side walls of the environmental test chamber 11 are lustrous stainless BA plates. The other possible examples include aluminum plates and gold-plated plates.

In the example of FIG. 5 where the side walls of the environmental test chamber 11 have improved light reflectance, the blocks with the irradiance range of ±10% relative to the irradiance at the center of the sample loading surface 21 generally covers the whole area of the sample loading surface 21. Meanwhile, blocks with the irradiance range of ±25% or more relative to the irradiance at the center occur only at the four corners of the measured field. Thus, the irradiance distribution over the sample loading surface 21 is within the irradiance range of ±25% relative to the center irradiance, which means the irradiance distribution of light from the fluorescent lamps over the sample loading surface 21 is more uniform.

In summary, with the photostability test system 10 of the present embodiment, the irradiance distribution of light from the fluorescent lamps 30 over the sample loading surface 21 is within the irradiance range of ±25% relative to the irradiance at the center of the sample loading surface 21, and hence, the irradiance distribution over the sample loading surface 21 is uniform. Therefore, a variation in irradiance of light applied to the samples S, which would be caused according to the sample loaded positions over the sample loading surface 21, can be prevented, and the photostability test can be carried out more precisely, improving the reliability of the test.

In the examples where the side walls of the environmental test chamber 11 are the reflectors 13 which have light reflectance of 20% or higher, rays of light emitted by the fluorescent lamps 30 are reflected by the reflectors 13, and both the primary and secondary reflections are appropriately applied to the samples S. These examples are advantageous in achieving more uniform irradiance distribution.

Other Embodiments

The above embodiment may have alternative structures as described below.

For example, the photostability test system 10 of the above embodiment may have an alternative layout of fluorescent lamps 30 as shown in FIG. 6.

Referring to FIG. 6, on each of the right and left sides of the environmental test chamber 11, three linear fluorescent lamps 30 are installed such that the longitudinal direction of the fluorescent lamps 30 is coincident with the system depth direction and that the fluorescent lamps 30 are placed side by side in the system width direction. These fluorescent lamps 30 are positioned generally at the center of the chamber 11 along the depthwise direction thereof.

Also, on each of the front and back sides of the environmental test chamber 11, three linear fluorescent lamps 30 are installed such that the longitudinal direction of the fluorescent lamps 30 is coincident with the system width direction and that the fluorescent lamps 30 are placed side by side in the system depth direction. These fluorescent lamps 30 are positioned generally at the center of the chamber 11 along the widthwise direction thereof. The fluorescent lamps 30 extending in the system depth direction and the fluorescent lamps 30 extending in the system width direction are positioned such that they do not overlap when viewed in the depth direction or the width direction.

With such a layout, the fluorescent lamps 30 are symmetrical with respect to the depth direction and the width direction and are rotationally symmetrical by 90° or 180° in a plane.

In a downsized system where the depth of the environmental test chamber 11 is shorter than that of the environmental test chamber 11 shown in FIG. 6, one of the three fluorescent lamps 30 provided on each of the front and back sides is removed, i.e., two fluorescent lamps 30 are placed side by side in the depth direction as shown in FIG. 7. In this case, the fluorescent lamps 30 are symmetrical with respect to the depth direction and the width direction and are rotationally symmetrical by 180° in a plane.

In the layout examples shown in FIGS. 6 and 7, the fluorescent lamps 30 extending in the system depth direction and the fluorescent lamps 30 extending in the system width direction are positioned such that they do not overlap when viewed in the width direction. This arrangement however increases the system size and thus may be modified as described below.

Figure 8:
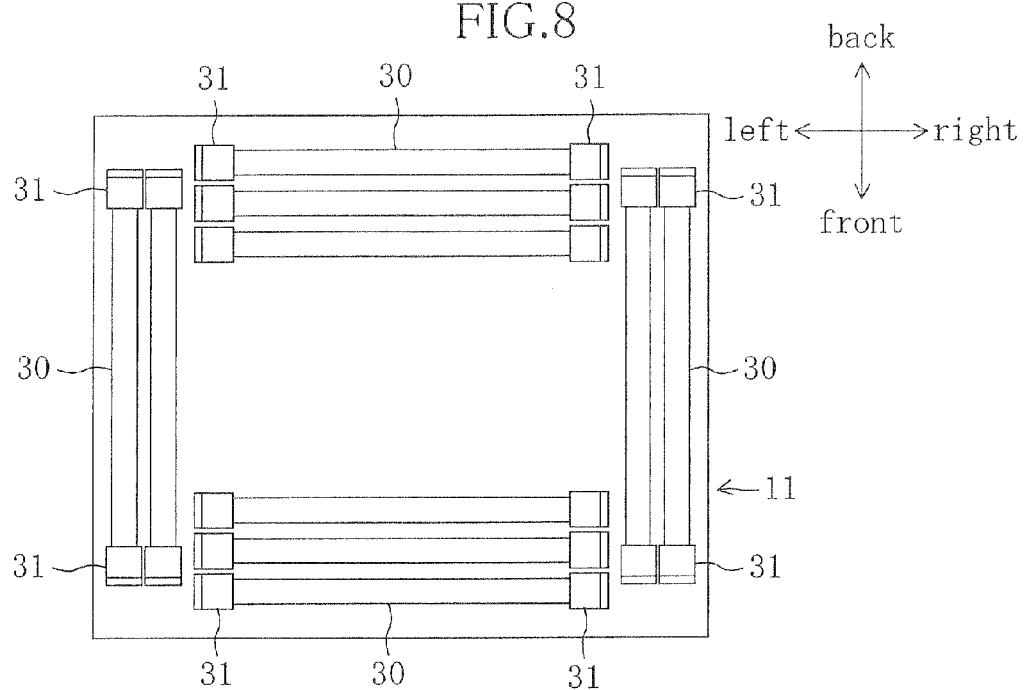
FIG. 8 is a plan view of still another embodiment, showing a layout example of fluorescent lamps.

Referring to FIG. 8, on each of the right and left sides of the environmental test chamber 11, two linear fluorescent lamps 30 are installed such that the longitudinal direction of the fluorescent lamps 30 is coincident with the system depth direction and that the fluorescent lamps 30 are placed side by side in the system width direction. These fluorescent lamps 30 are positioned generally at the center of the chamber 11 along the depthwise direction thereof.

On each of the front and back sides of the environmental test chamber 11, three linear fluorescent lamps 30 are installed such that the longitudinal direction of the fluorescent lamps 30 is coincident with the system width direction and that the fluorescent lamps 30 are placed side by side in the system depth direction. These fluorescent lamps 30 are positioned generally at the center of the chamber 11 along the widthwise direction thereof. The fluorescent lamps 30 extending in the system width direction are positioned closer to the center of the sample loading surface 21 as compared with the layouts of FIGS. 6 and 7. The fluorescent lamps 30 extending in the system depth direction and the fluorescent lamps 30 extending in the system width direction are positioned such that they overlap when viewed in the width direction. In this case, the fluorescent lamps 30 are symmetrical with respect to the depth direction and the width direction and are rotationally symmetrical by 180° in a plane.

Figure 9:
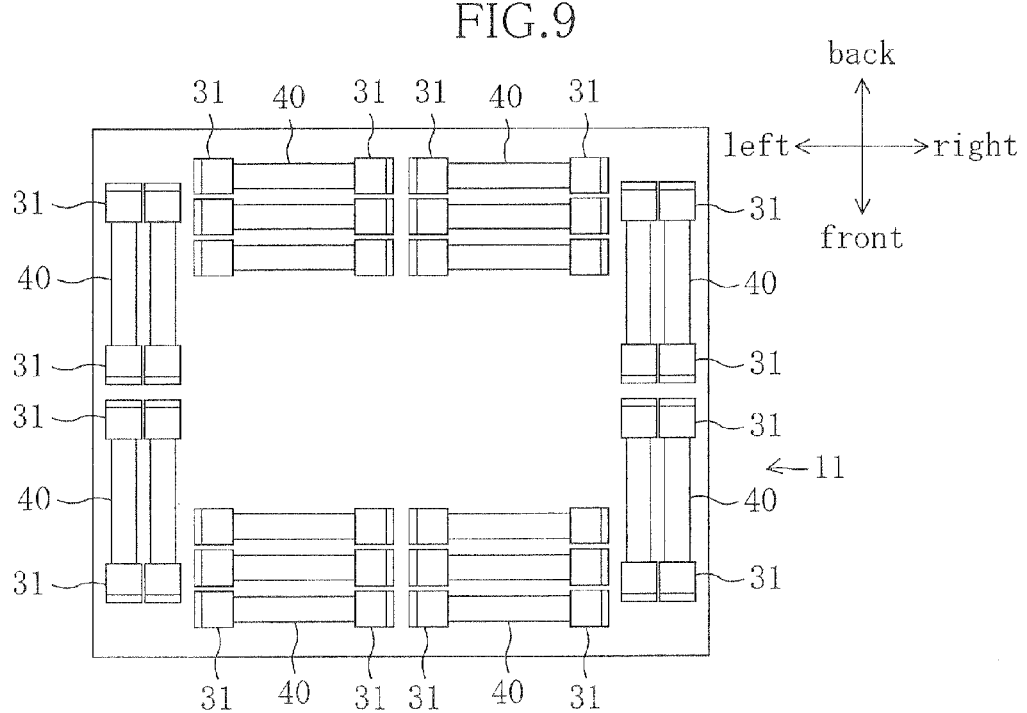
FIG. 9 is a plan view of still another embodiment, showing a layout example of fluorescent lamps.

FIG. 9 shows a layout example which uses shorter fluorescent lamps 40 than the fluorescent lamps 30 of FIG. 8. Referring to FIG. 9, on each of the right and left sides of the environmental test chamber 11, two couples of linear fluorescent lamps 40 are placed side by side in the system width direction such that each couple of the fluorescent lamps 40 are coaxially aligned in the system depth direction.

On each of the front and back sides of the environmental test chamber 11, three couples of linear fluorescent lamps 40 are placed side by side in the system depth direction such that each couple of the fluorescent lamps 40 are coaxially aligned in the system width direction. In this case, the fluorescent lamps 30 are symmetrical with respect to the depth direction and the width direction and are rotationally symmetrical by 180° in a plane.

Figure 10:
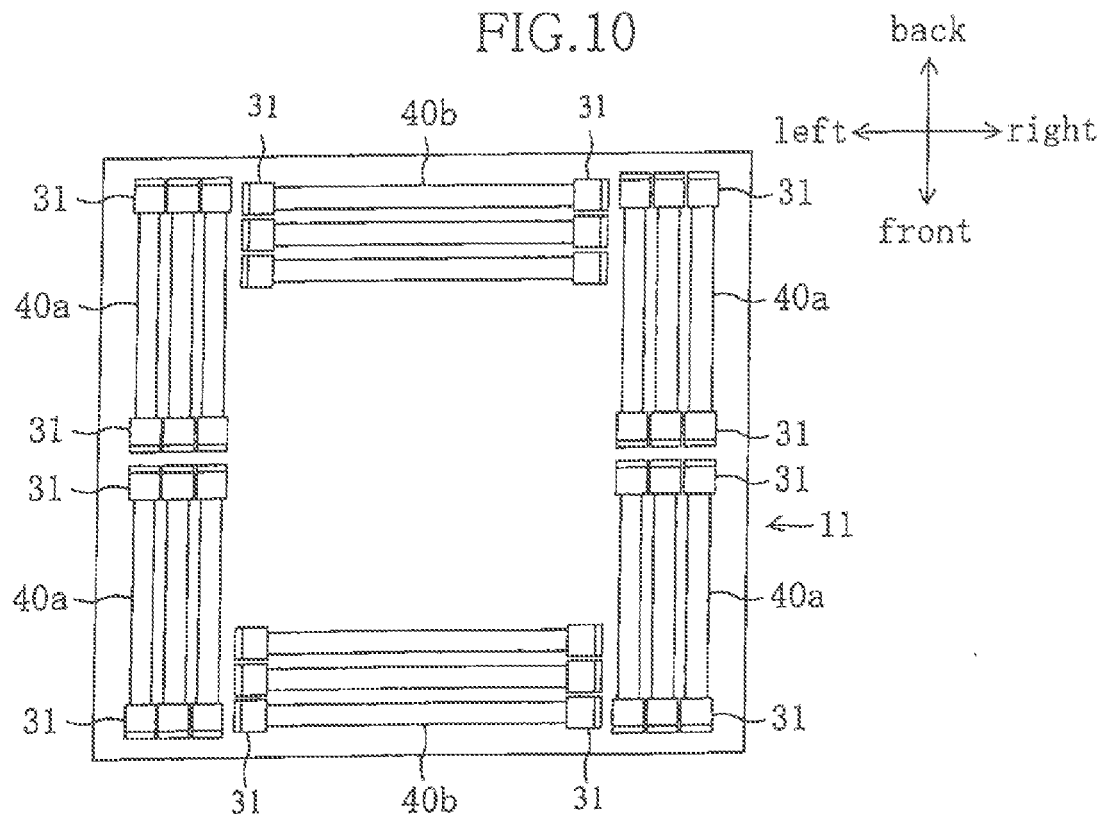
FIG. 10 is a plan view of still another embodiment, showing a layout example of fluorescent lamps.

In the example of FIG. 10, fluorescent lamps 40a provided on the right and left sides of the environmental test chamber 11 and fluorescent lamps 40b provided on the front and back sides have different lengths.

Referring to FIG. 10, on each of the right and left sides of the environmental test chamber 11, three couples of linear fluorescent lamps 40a are placed side by side in the system width direction such that each couple of the fluorescent lamps 40a are coaxially aligned in the system depth direction.

On each of the front and back sides of the environmental test chamber 11, three linear fluorescent lamps 40b are installed such that the longitudinal direction of the fluorescent lamps 40b is coincident with the system width direction and that the fluorescent lamps 40b are placed side by side in the system depth direction. In this case, the fluorescent lamps 40a and 40b are symmetrical with respect to the depth direction and the width direction and are rotationally symmetrical by 180° in a plane.

In the example of FIG. 10, the fluorescent lamps 40a provided on the right and left sides of the environmental test chamber 11 are shorter than the fluorescent lamps 40b provided on the front and back sides, although the present invention is not limited to this example.

Figure 11:
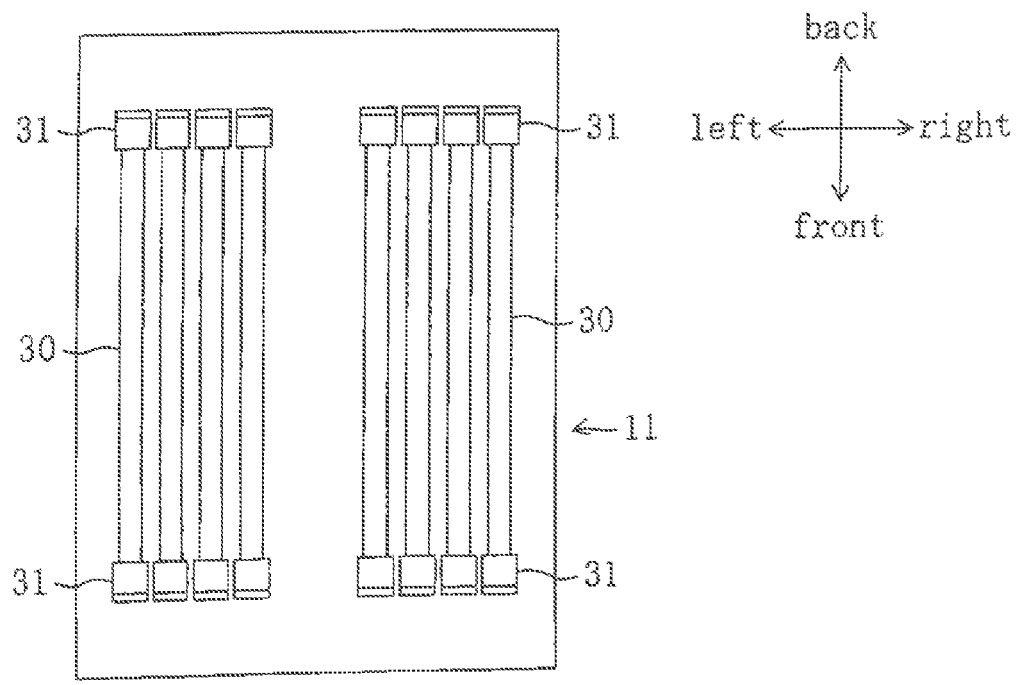
FIG. 11 is a plan view of still another embodiment, showing a layout example of fluorescent lamps.

FIG. 11 shows another decentered layout example where a plurality of fluorescent lamps 30 are placed in a peripheral part of the upper space of the environmental test chamber 11.

In this example, the fluorescent lamps 30 are placed side by side in the environmental test chamber 11 with a blank at the central region of the environmental test chamber 11 as if some fluorescent lamps 30 were removed therefrom.

Referring to FIG. 11, on each of the right and left sides of the environmental test chamber 11, four linear fluorescent lamps 30 are installed such that the longitudinal direction of the fluorescent lamps 30 is coincident with the system depth direction and that the fluorescent lamps 30 are placed side by side in the system width direction. These fluorescent lamps 30 are positioned generally at the center of the chamber 11 along the depthwise direction thereof. In this case, the fluorescent lamps 40a and 40b are symmetrical with respect to the depth direction and the width direction and are rotationally symmetrical by 180° in a plane.

With such an arrangement, the fluorescent lamps 30 can be in a decentered layout so as to be placed in a peripheral part of the upper space of the environmental test chamber 11. This layout also advantageously achieves, as do the aforementioned embodiments, uniform irradiance distribution of light from the fluorescent lamps 30 over the sample loading surface 21 as compared with the example where the fluorescent lamps 30 are placed side by side throughout the upper space of the environmental test chamber 11. Alternatively, the number of fluorescent lamps 30 may further be reduced in the central region of the sample loading surface 21 such that the blank area is increased.

Figure 12:
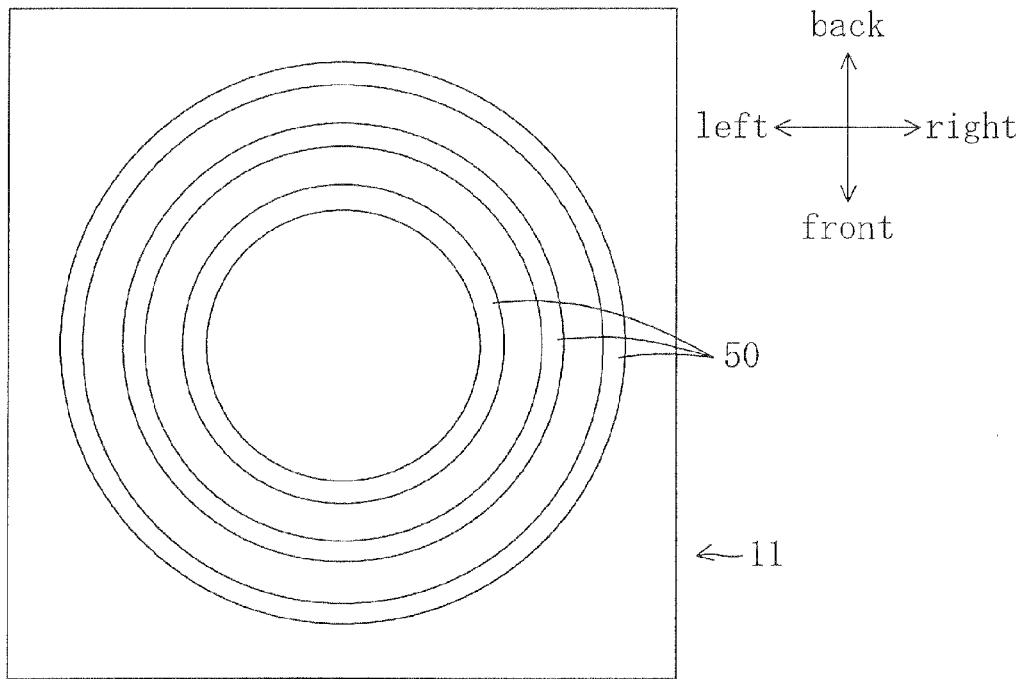
FIG. 12 is a plan view of still another embodiment, showing a layout example of fluorescent lamps.

Alternatively, circular fluorescent lamps 50 may be used as shown in FIG. 12. Specifically, the three circular fluorescent lamps 50 having different diameters are concentrically placed with the center of the sample loading surface 21 being the concentric center. In this case, the fluorescent lamps 50 are symmetrical with respect to the depth direction and the width direction and are rotationally symmetrical by 90° and 180° in a plane.

Figure 13:
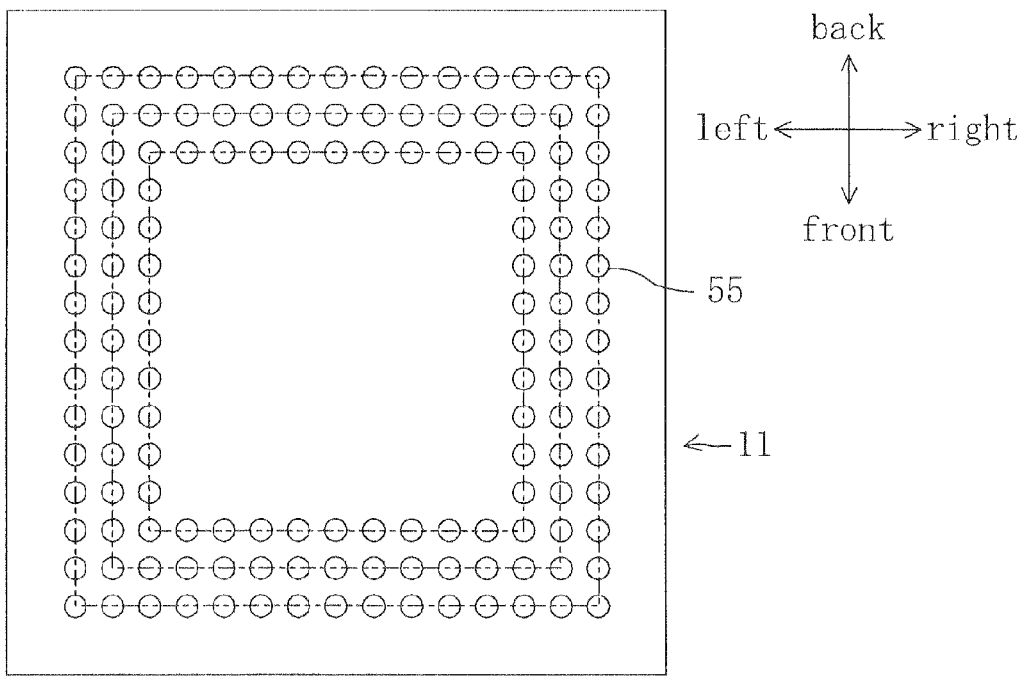
FIG. 13 is a plan view of still another embodiment, showing a layout example of fluorescent lamps.
Figure 14:
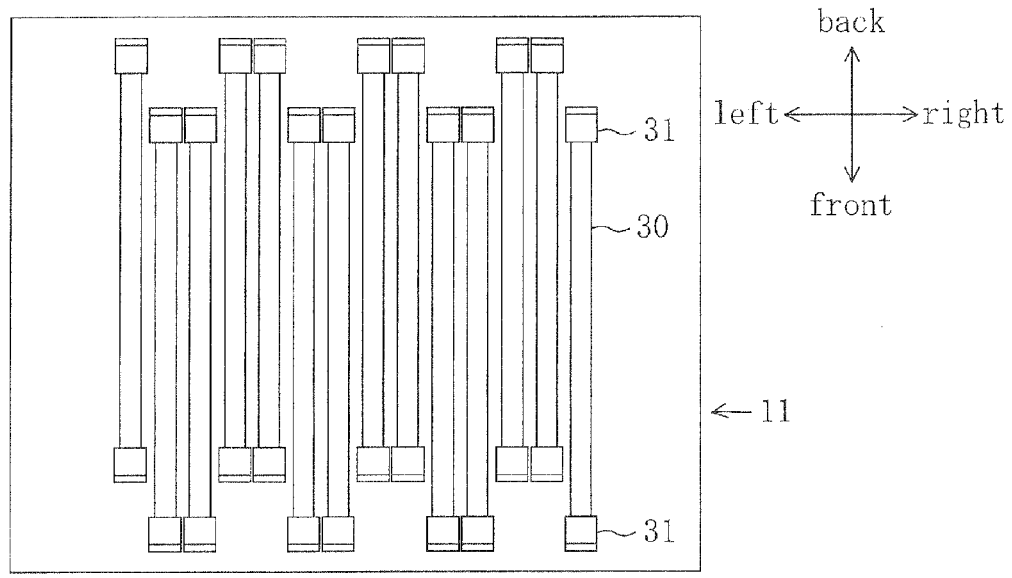
FIG. 14 is a plan view of a conventional photostability test system, showing a layout example of fluorescent lamps.
Figure 15:
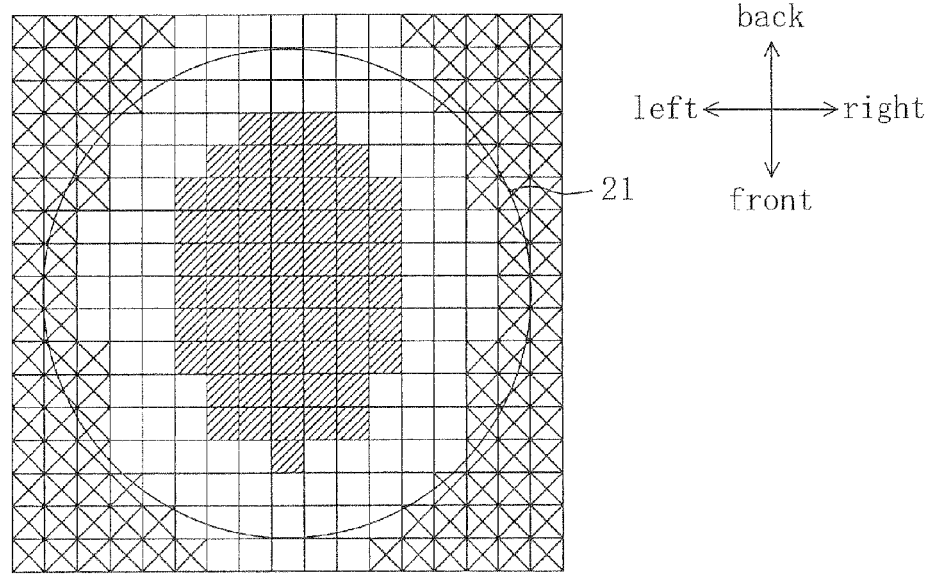
FIG. 15 is a plan view showing the irradiance distribution of light from the fluorescent lamps over a sample loading surface in the conventional photostability test system.

Alternatively, the example of FIG. 13 may be possible where a plurality of bulb-shaped fluorescent lamps 55, each of which forms a dot, are provided with intervals. Specifically, the fluorescent lamps 55 are aligned with intervals along the four sides of three imaginary squares of different sizes which are concentrically placed with the center of the sample loading surface 21 being the concentric center.

Note that in the example of FIG. 13 the fluorescent lamps 55, each of which forms a dot, are not limited to bulb-shaped fluorescent lamps. For example, a different type of dot light source, such as LED (Light Emitting Diode) and HID lamps (High Intensity Discharge Lamps), may be used instead.

In this case, the fluorescent lamps 55 are symmetrical with respect to the depth direction and the width direction and are rotationally symmetrical by 90° and 180° in a plane.

Note that the number of fluorescent lamps is not limited to the numbers described with reference to the drawings but may be increased or decreased according to, for example, the size of the system.

Industrial Applicability

As described above, the present invention achieves a highly-practical effect, uniform irradiance distribution of light from fluorescent lamps over a sample loading surface, and is therefore extremely useful and has high industrial applicability.

The invention claimed is:
1. A photostability test system, comprising:
a system enclosure which has an environmental test chamber in the form of a box;
a sample table provided in a lower part of the environmental test chamber, the sample table having a sample loading surface on which a sample is to be loaded; and
a plurality of rod-like light sources provided in an upper part of the environmental test chamber, the fluorescent lamps being placed above the sample loading surface and directed toward the sample loading surface for irradiating a sample loaded on the sample loading surface,
wherein, in an upper space of the environment test chamber, the rod-like light sources, which extend in a front-back direction of the environmental test chamber and which are arranged in parallel in a right-left direction, are provided on one end side and another other end side in the right-left direction of the environmental chamber,
front side ends of the rod-like light sources arranged on the one end side of the environmental test chamber are installed closer to a front of the environmental test chamber, and a gap is provided between a back of the environmental test chamber and back side ends of the rod-like light sources,
back side ends of the light sources arranged on another other side of the environmental test chamber are installed closer to the back of the environmental test chamber, and a gap is provided between the front of the environmental test chamber and the front side ends of the rod-like light sources,
in the gaps at a front side and a back side of the environmental test chamber, the rod-like light sources, which extend in the right-left direction of the environmental test chamber and which are arranged in parallel in the front-back direction, are provided, and
an irradiance distribution of light from the rod-like light sources over the sample loading surface is in the range of ±25% relative to an irradiance at a center of the sample loading surface.
2. The photostability test system of claim 1, wherein a side wall of the environmental test chamber is formed by a reflector which has a light reflectance of 20% or higher.

* * * * *